(12) United States Patent
Elfakhri et al.

(10) Patent No.: US 11,191,342 B2
(45) Date of Patent: Dec. 7, 2021

(54) TECHNIQUES FOR IDENTIFYING SKIN COLOR IN IMAGES HAVING UNCONTROLLED LIGHTING CONDITIONS

(71) Applicant: L'Oreal, Paris (FR)

(72) Inventors: Christine Elfakhri, Brooklyn, NY (US); Florent Valceschini, Jersey City, NJ (US); Loic Tran, Vincennes (FR); Matthieu Perrot, Orsay (FR); Robin Kips, Paris (FR); Emmanuel Malherbe, Paris (FR)

(73) Assignee: L'Oreal, Paris (FR)

( * ) Notice: Subject to any disclaimer, the term of this patent is extended or adjusted under 35 U.S.C. 154(b) by 90 days.

(21) Appl. No.: 16/516,080

(22) Filed: Jul. 18, 2019

(65) Prior Publication Data

US 2021/0015240 A1 Jan. 21, 2021

(51) Int. Cl.
| | | |
|---|---|---|
| *A45D 44/00* | (2006.01) | |
| *G06N 20/00* | (2019.01) | |
| *A61B 5/00* | (2006.01) | |
| *B44D 3/00* | (2006.01) | |
| *G01J 3/46* | (2006.01) | |

(52) U.S. Cl.
CPC ............ *A45D 44/005* (2013.01); *A61B 5/441* (2013.01); *B44D 3/003* (2013.01); *G01J 3/46* (2013.01); *G06N 20/00* (2019.01); *A45D 2044/007* (2013.01); *A61B 5/0077* (2013.01)

(58) Field of Classification Search
None
See application file for complete search history.

(56) References Cited

U.S. PATENT DOCUMENTS

| | | |
|---|---|---|
| 6,437,866 B1 | 8/2002 | Flynn |
| 8,830,468 B2 | 9/2014 | Igarashi |
| 2019/0034700 A1* | 1/2019 | Xie .................. G06T 7/246 |

OTHER PUBLICATIONS

Borza, D., et al. "Automatic Skin Tone Extraction for Visagism Applications," Proceedings of the 13th International Joint Conference on Computer Vision, Imaging and Computer Graphics Theory and Applications, Madeira, Portugal, Jan. 27-Jan. 29, 2018, vol. 4, pp. 466-473.

Chang, C., et al. "Robust Skin Type Classification Using Convolutional Neural Networks" 2018 13th IEEE Conference on Industrial Electronics and Applications (ICIEA), IEEE, Wuhan, China, May 31-Jun. 2, pp. 1-5.

(Continued)

*Primary Examiner* — Vikkram Bali
(74) *Attorney, Agent, or Firm* — Christensen O'Connor Johnson Kindness PLLC (57) ABSTRACT

In some embodiments of the present disclosure, one or more machine learning models are trained to accurately estimate skin color in one or more images regardless of the lighting conditions. In some embodiments, the models can then be used to estimate a skin color in a new image, and that estimated skin color can be used for a variety of purposes. For example, the skin color may be used to generate a recommendation for a foundation shade that accurately matches the skin color, or a recommendation for another cosmetic product that is complimentary with the estimated skin color. Thus, the need for an in-person test of the product is eliminated.

18 Claims, 6 Drawing Sheets

(56) References Cited

OTHER PUBLICATIONS

Buzzelli, M., et al. "Learning Illuminant Estimation from Object Recognition" IEEE 2018 International Conference on Image Processing (ICIP 2018), IEEE, Athens, Greece, Oct. 7-10, pp. 1-5.
International Search Report and Written Opinion dated Oct. 22, 2020, issued in corresponding International Application No. PCT/US2020/041350, filed Jul. 9, 2020, 16 pages.

* cited by examiner

TECHNIQUES FOR IDENTIFYING SKIN COLOR IN IMAGES HAVING UNCONTROLLED LIGHTING CONDITIONS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a method of training a machine learning model to estimate a skin color of a face in an image is provided. A computing device receives at least one training image that includes a face of a training subject. The computing device receives tagging information for the at least one training image. The computing device adds the at least one training image and the tagging information to a training data store. The computing device trains the machine learning model to determine skin colors of faces using information stored in the training data store.

In some embodiments, a method of using one or more machine learning models to estimate a skin color of a face is provided. A computing device receives at least one image that includes a face of a live subject. The computing device processes the at least one image using at least one machine learning model to obtain a determination of a skin color. The computing device presents the skin color.

In some embodiments, a system is provided. The system comprises a skin color prediction unit including computational circuitry configured to receive at least one training image that includes a face of a training subject; receive tagging information for the at least one training image; add the at least one training image and the tagging information to a training data store; and train the machine learning model to determine skin colors of faces using the training data set.

In some embodiments, a system is provided. The system comprises a skin color prediction unit and a predicted skin color unit. The skin color prediction unit includes computational circuitry configured to generate a pixel-wise prediction score for skin color of a face in an image using one or more convolutional neural network image classifiers. The predicted skin color unit includes computational circuitry configured to generate a virtual display of a predicted skin color of a user responsive to one or more inputs based on the prediction scores for the skin color of the face.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Shopping for products online, including via mobile computing devices, is a convenient way for consumers to browse and obtain products. In addition to having large catalogs of items available at the click of a mouse or a tap of a finger, various technologies exist to provide online shoppers with a wide range of recommendations for products that they may be interested in based on other products they are interested in, their purchase history, their reviews of other products, the purchase history and reviews of other shoppers, and so on.

However, there are certain types of products for which an in-person experience has been difficult to replace with an online interaction. For example, beauty products such as foundation or other makeup are difficult to browse online, and are difficult to recommend in an automated manner. This is primarily because the characteristic of the consumer that would be the most relevant basis of a recommendation—facial skin color—is difficult to estimate in an automated way. Even if an image or video of the consumer is captured, that image cannot currently be used to reliably determine a skin color due to technical deficiencies in the processing of images from uncontrolled environments. Inconsistent lighting conditions between locations would lead to different colors being reproduced within the image or video in different locations, and so the determined skin color would be different based on the lighting conditions. What is desired are techniques that can overcome these technical limitations in order to accurately estimate a skin color in an image regardless of lighting conditions.

In some embodiments of the present disclosure, one or more machine learning models are trained to accurately estimate skin color in one or more images regardless of the lighting conditions. In some embodiments, the models can then be used to estimate a skin color in a new image, and that estimated skin color can be used for a variety of purposes. For example, the skin color may be used to generate a recommendation for a foundation shade that accurately matches the skin color, or a recommendation for another cosmetic product that is complimentary with the estimated skin color. Thus, the need for an in-person test of the product is eliminated, and the benefits of an online shopping experience can be extended to these new products that are heavily color-match dependent.

Figure 1:
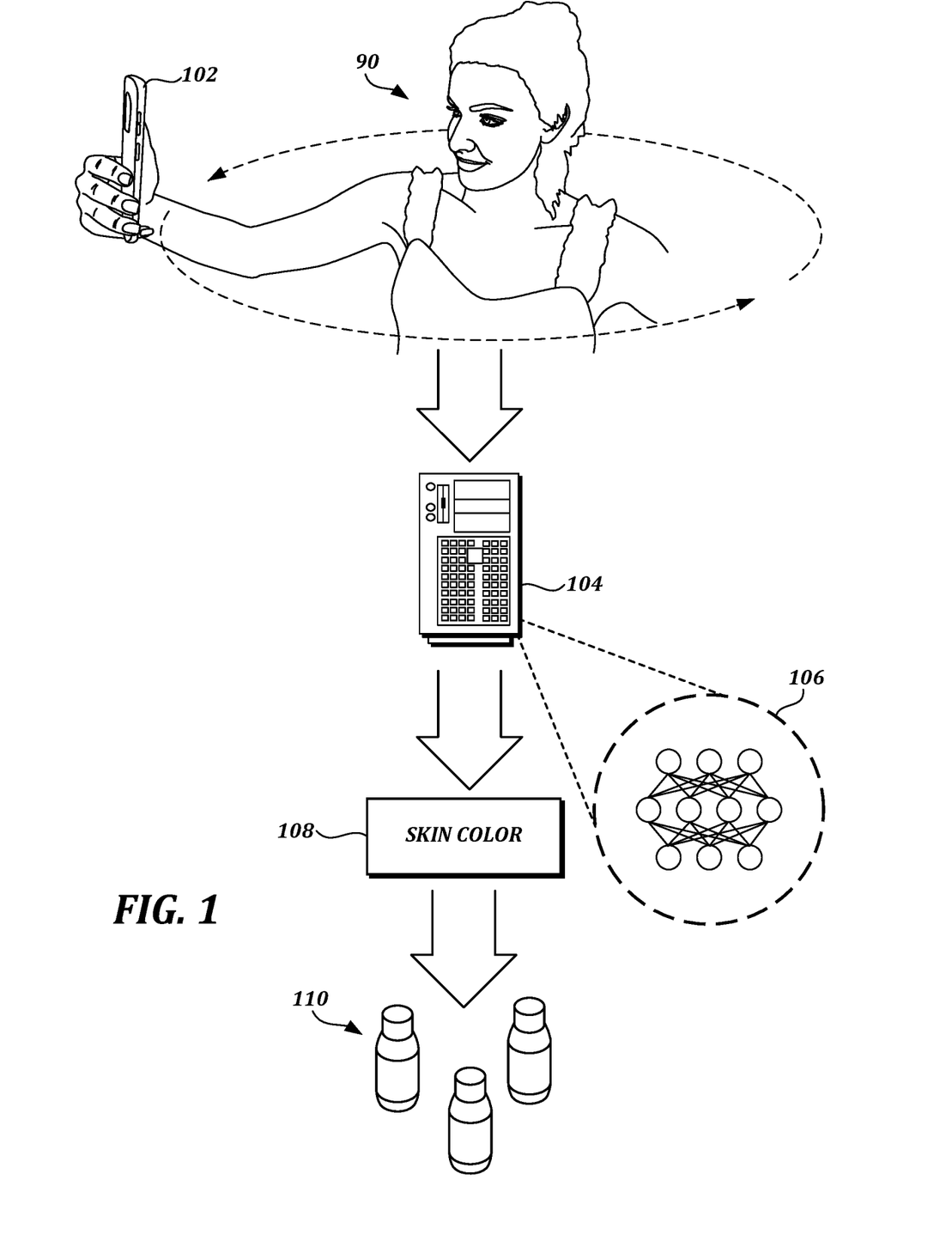
FIG. 1 is a schematic illustration of a non-limiting example embodiment of a system that uses at least one machine learning model to generate an automatic estimation of a skin color according to various aspects of the present disclosure.

FIG. 1 is a schematic illustration of a non-limiting example embodiment of a system that uses at least one machine learning model to generate an automatic estimation of a skin color according to various aspects of the present disclosure. As shown, a user 90 has a mobile computing device 102. The user 90 captures an image of their face with the mobile computing device 102. The user 90 may be in any type of location, and therefore the lighting conditions under which the image is captured may be unknown. The mobile computing device 90 transmits the image to a skin color determination device 104. The skin color determination device 104 uses one or more machine learning models 106 to determine the skin color 108 based on the image. The skin color 108 may then be used to make recommendations of one or more products 110 that would complement or otherwise be appropriate for the skin color 108.

In some embodiments, the mobile computing device 90 may transmit more than one image to the skin color determination device 104. In some embodiments, multiple images may be captured by capturing a video instead of a solitary image, and lighting conditions may be changed by moving the mobile computing device 102 while capturing the video. For example, the user 90 may configure the mobile computing device 102 to capture a video using a front-facing camera (also known as a "selfie" camera), and may spin while holding the mobile computing device 102 in a "selfie" position in order to change the lighting conditions experienced. By providing multiple images in different lighting conditions, the machine learning model 106 may be used to generate multiple skin color 108 determinations, which can then be averaged or otherwise combined to improve the accuracy of the determination.

Figure 2:
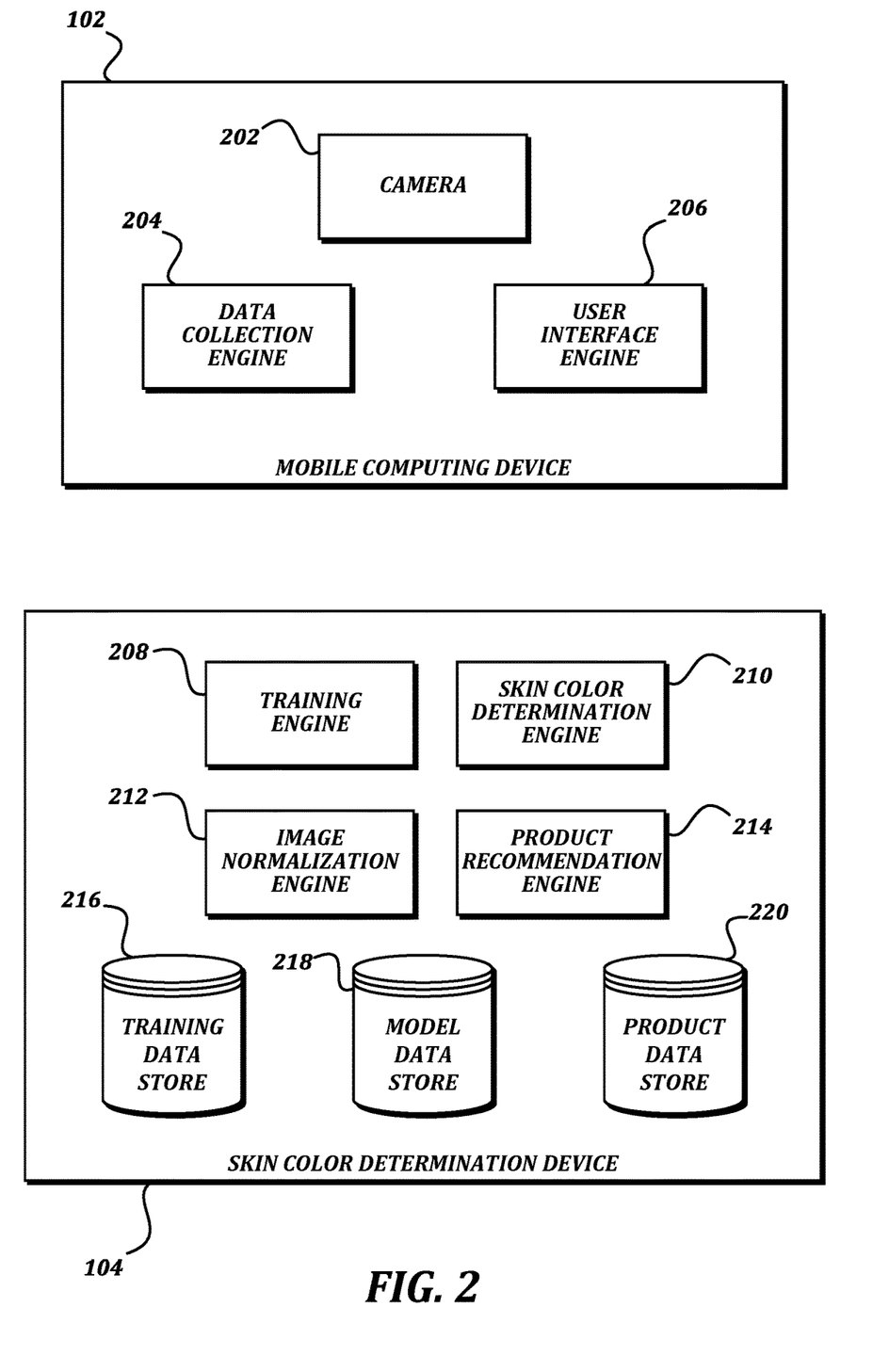
FIG. 2 is a block diagram that illustrates non-limiting example embodiments of a mobile computing device and a skin color determination device according to various aspects of the present disclosure.

FIG. 2 is a block diagram that illustrates non-limiting example embodiments of a mobile computing device and a skin color determination device according to various aspects of the present disclosure. As discussed above, the mobile computing device 102 is used to capture an image of a user 90, and the mobile computing device 102 transmits the image to the skin color determination device 104 for determining a skin color of the user 90. The mobile computing device 102 and the skin color determination device 104 may communicate using any suitable communication technology, such as wireless communication technologies including but not limited to Wi-Fi, Wi-MAX, Bluetooth, 2G, 3G, 4G, 5G, and LTE; or wired communication technologies including but not limited to Ethernet, FireWire, and USB. In some embodiments, the communication between the mobile computing device 102 and the skin color determination device 104 may occur at least in part over the Internet.

In some embodiments, the mobile computing device 102 is a smartphone, a tablet computing device, or another computing device having at least the illustrated components. In the illustrated embodiment, the mobile computing device 102 includes a camera 202, a data collection engine 204, and a user interface engine 206. In some embodiments, the camera 202 is configured to capture images. In some embodiments, the mobile computing device 102 may include multiple cameras, including but not limited to a front-facing camera and a rear-facing camera. In some embodiments, the front-facing camera (that is, a camera located on a same face of the mobile computing device 102 as a display of the mobile computing device 102) may be used as the camera 202 for capturing images.

In some embodiments, the data collection engine 204 is configured to use the camera 202 to capture images of the user 90, and may also be configured to capture training images for training the machine learning model 106. In some embodiments, the user interface engine 206 is configured to present a user interface for collecting skin color information for a training subject.

In some embodiments, the skin color determination device 104 is a desktop computing device, a server computing device, a cloud computing device, or another computing device that provides the illustrated components. In the illustrated embodiment, the skin color determination device 104 includes a training engine 208, a skin color determination engine 210, an image normalization engine 212, a product recommendation engine 214. In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

As shown, the skin color determination device 104 also includes a training data store 216, a model data store 218, and a product data store 220. As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

In some embodiments, the training engine 208 is configured to access training data stored in the training data store 216 and to use the training data to generate one or more machine learning models. The training engine 208 may store the generated machine learning models in the model data store 218. In some embodiments, the skin color determination engine 210 is configured to use one or more machine learning models stored in the model data store 218 to process images in order to estimate a skin color depicted in the images. In some embodiments, the image normalization engine 212 is configured to pre-process images before they are provided to the training engine 208 or the skin color determination engine 210 in order to improve the accuracy of the determinations made. In some embodiments, the product recommendation engine 214 is configured to recommend one or more products stored in the product data store 220 based on a determined skin color.

Though FIG. 2 illustrates various components as being provided by the mobile computing device 102 or the skin color determination device 104, in some embodiments, the layout of the components may be different. For example, in some embodiments, the skin color determination engine 210 and model data store 218 may be present on the mobile computing device 102 so that the mobile computing device 102 can determine skin colors in images captured by the camera 202 without transmitting the images to the skin color determination device 104. As another example, in some embodiments, all of the components may be provided by a single computing device. As yet another example, in some embodiments, multiple computing devices may work together to provide the functionality illustrated as being provided by the skin color determination device 104.

Figure 3:
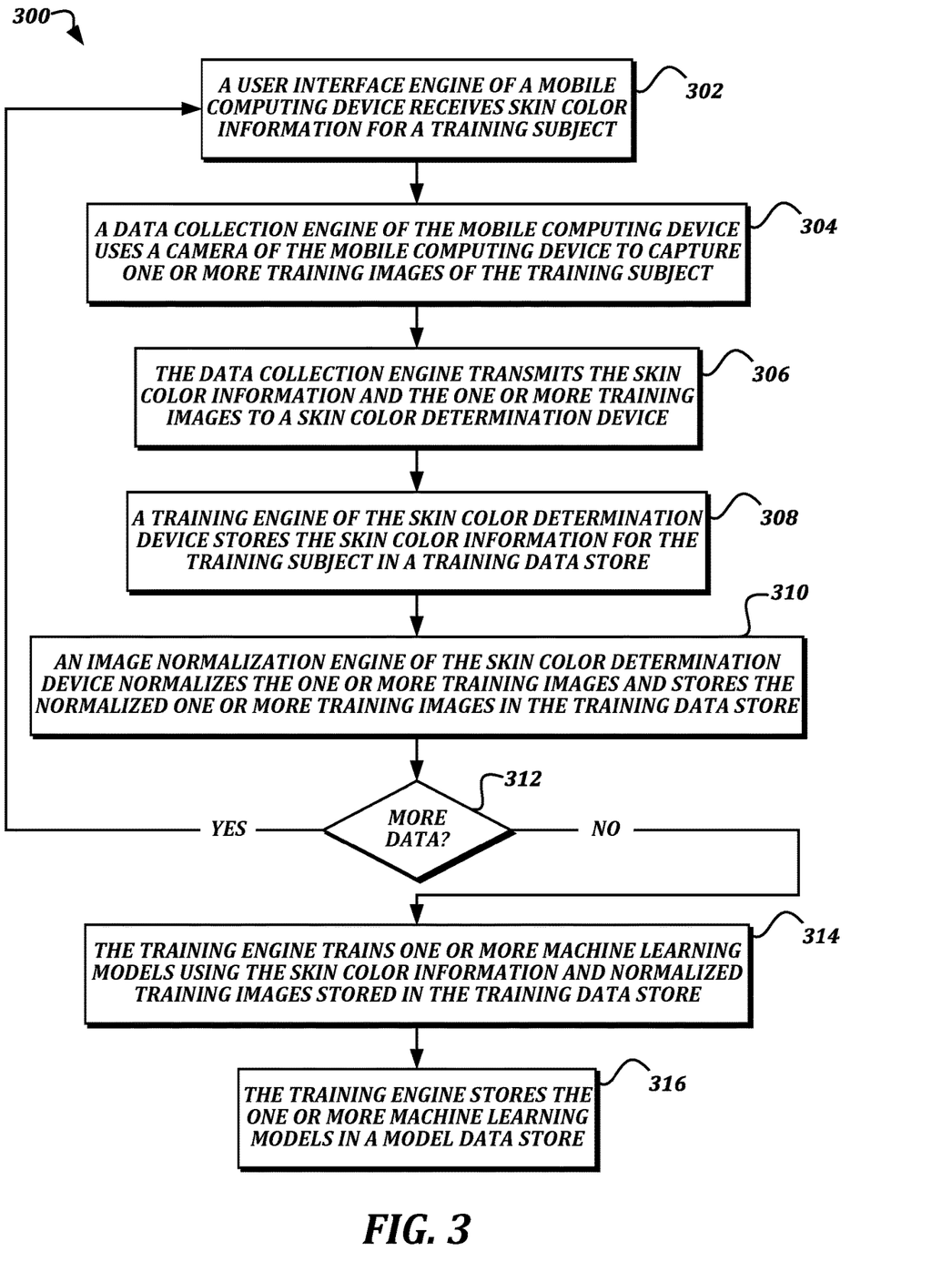
FIG. 3 is a flowchart that illustrates a non-limiting example embodiment of a method of training a machine learning model to estimate a skin color of a face in an image according to various aspects of the present disclosure.

FIG. 3 is a flowchart that illustrates a non-limiting example embodiment of a method of training a machine learning model to estimate a skin color of a face in an image according to various aspects of the present disclosure. In the method 300, a set of training data is collected, and the skin color determination device 104 uses the training data to generate one or more machine learning models that can then be used to estimate skin color in images despite uncontrolled lighting conditions.

At block 302, a user interface engine 206 of a mobile computing device 102 receives skin color information for a training subject. This skin color information is used as ground truth or tagging information for images that will be captured of the training subject. In some embodiments, the user interface engine 206 presents an interface that allows the skin color information to be input by a user. In some embodiments, the skin color information may be collected by a user using an industry-standard technique for determining a skin color, such as a comparison with a color chart or a value determined by a spectrophotometer. In some embodiments, instead of using a user interface, the skin color information may be collected electronically from a device such as a spectrophotometer. In some embodiments, a portion of the image may depict a color reference chart. In such embodiments, applying a color correction to the image based on the depiction of the color reference chart may allow the skin color information to be determined from the image itself.

At block 304, a data collection engine 204 of the mobile computing device 102 uses a camera 202 of the mobile computing device 102 to capture one or more training images of the training subject. In some embodiments, a front-facing camera 202 of a mobile computing device 102 held by the training subject may be used to capture the training images. In some embodiments, the training images may be collected in different lighting conditions. In some embodiments, the training images may be individual images. In some embodiments, multiple training images may be collected by recording a video with the camera 202. In some embodiments, the lighting conditions may be varied by having the training subject move while recording the video (such as spinning in a circle). Multiple training images may then be generated by extracting individual frames from the video. Capturing a video in order to generate multiple training images may be beneficial, at least because it will greatly increase the efficiency of generating a large amount of training data with different lighting conditions.

At block 306, the data collection engine 204 transmits the skin color information and the one or more training images to a skin color determination device 104. The transmission may take place using any suitable wired or wireless communication technology, as discussed above. At block 308, a training engine 208 of the skin color determination device 104 stores the skin color information for the training subject in a training data store 216. The skin color information may be used as tagging data that indicates a desired result of the processing of the training images.

At block 310, an image normalization engine 212 of the skin color determination device 104 normalizes the one or more training images and stores the normalized one or more training images in the training data store 216. In some embodiments, the normalization of the training images is optional, and the remainder of the method 300 may operate on the raw, un-normalized training images. In some embodiments, the normalization of the one or more training images can help improve the accuracy of the machine learning model.

Figure 4:
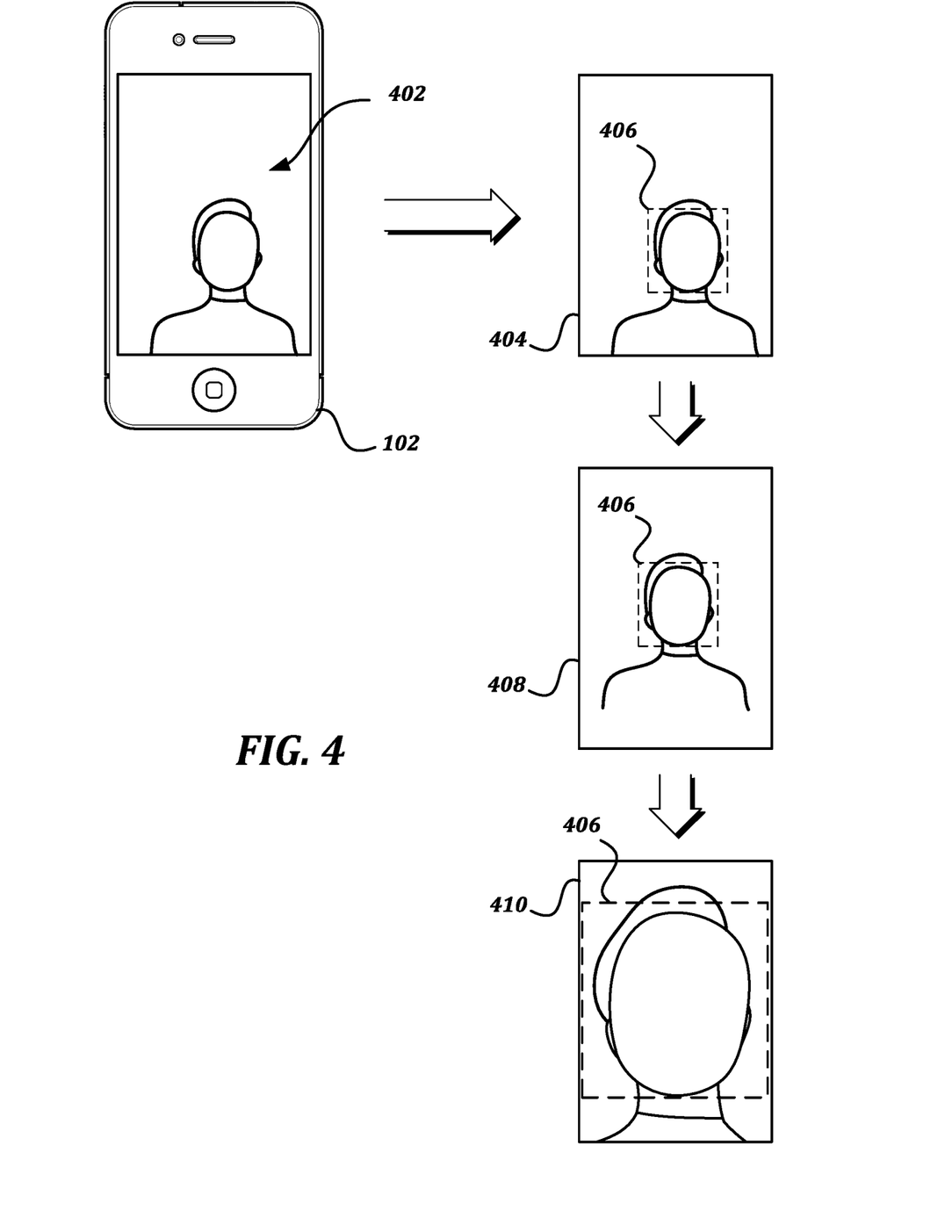
FIG. 4 is a schematic drawing that illustrates a non-limiting example embodiment of normalization of an image that includes a face according to various aspects of the present disclosure.

FIG. 4 is a schematic drawing that illustrates a non-limiting example embodiment of normalization of an image that includes a face according to various aspects of the present disclosure. As shown, the mobile computing device 102 has captured an image 402 of the training subject, and is presenting the image 402 on a display device of the mobile computing device 102. The image 402 includes an off-center face that takes up only a small portion of the overall image 402. As such, it may be difficult to train a machine learning model to estimate a skin color based on the image 402. It may be desirable to reduce the amount of non-face area in the image, and to place the face area of the image in a consistent location.

In a first normalization action 404, the image normalization engine 212 uses a face detection algorithm to detect the portion of the image 404 that depicts the face. The image normalization engine 212 may use the face detection algorithm to find a bounding box 406 that includes the face. In a second normalization action 408, the image normalization engine 212 may alter the image 408 to center the bounding box 406 within the image 408. In a third normalization action 410, the image normalization engine 212 may zoom the image 410 to cause the bounding box 406 to be as large as possible within the image 410. By conducting the normalization actions, the image normalization engine 212 can reduce differences in layout and size between multiple images, and can therefore improve the training and accuracy of the machine learning model. In some embodiments, different normalization actions may occur. For example, in some embodiments, instead of centering and zooming the bounding box 406, the image normalization engine 212 may crop the image to the bounding box 406. As another example, in some embodiments, the image normalization engine 212 may reduce or increase the bit depth, or may undersample or oversample the pixels of the image in order to match other images collected by different cameras 202 or different mobile computing devices 102.

Returning to FIG. 3, at decision block 312, a determination is made regarding whether more training data is to be collected. This determination may be based on a predetermined threshold amount of training data that is considered by an administrator to be enough for training the machine learning model. If it is determined that more training data is to be collected, then the result of decision block 312 is YES, and the method 300 returns to block 302 to collect training data for a new training subject. Otherwise, if enough training data has been collected, then the result of decision block 312 is NO.

At block 314, the training engine 208 trains one or more machine learning models using the skin color information and normalized training images stored in the training data store. In some embodiments, a first machine learning model may be trained to take the normalized training images as input and to output an estimated illuminant color, and a second machine learning model may be trained to take the normalized training images and estimated illuminant color as input, and to output an estimated skin color. In some embodiments, a single machine learning model may be trained to take the normalized training images as input and to output an estimated skin color. Using the first machine learning model and second machine learning model may be beneficial in that the estimated illuminant color could be used to correct the presented color of the image or to detect the colors of other objects in the image, while using the single machine learning model may be beneficial in terms of reducing training time and complexity. In some embodiments, the machine learning models may be neural networks, including but not limited to feedforward neural networks, convolutional neural networks, and recurrent neural networks. In some embodiments, any suitable training technique may be used, including but not limited to gradient descent (including but not limited to stochastic, batch, and mini-batch gradient descent).

At block 316, the training engine 208 stores the one or machine learning models in a model data store 218. In some embodiments, portions of the model data store 218 may be present on the mobile computing device 102 or another device, in which case the training engine 208 may transmit the one or more machine learning models to the other devices that hold portions of the model data store 218.

Figure 5:
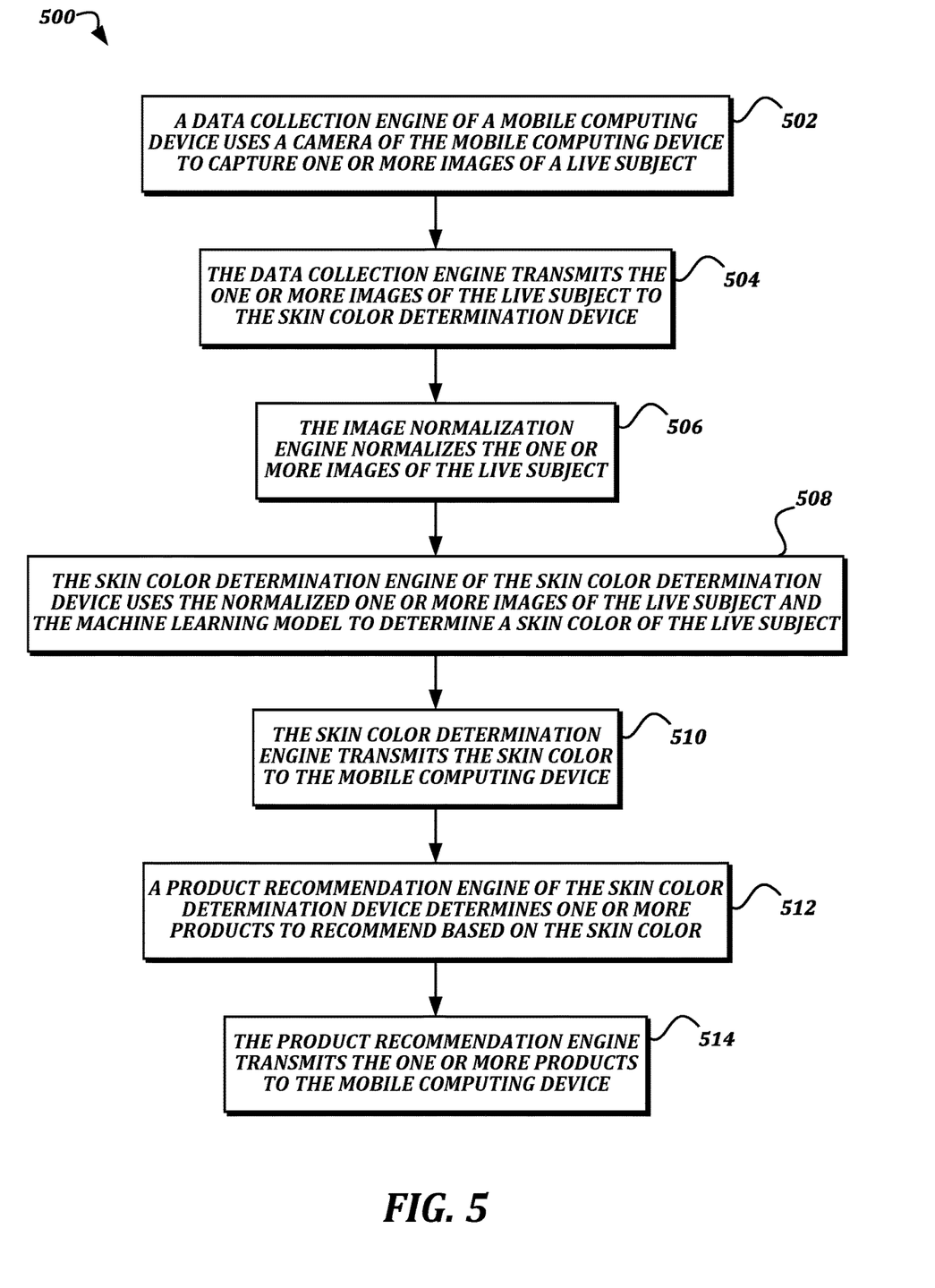
FIG. 5 is a flowchart that illustrates a non-limiting example embodiment of a method of using a machine learning model to estimate a skin color of a face in an image according to various aspects of the present disclosure.

FIG. 5 is a flowchart that illustrates a non-limiting example embodiment of a method of using a machine learning model to estimate a skin color of a face in an image according to various aspects of the present disclosure. In the method 500, the skin color determination device 104 uses the one or more machine learning models generated by the method 300 discussed above in order to estimate a skin color in an image of a live subject. The subject is referred to as a "live subject" in method 500 in order to distinguish the subject from the training subjects analyzed in the method 300. While ground truth skin color information was available for the training subjects, such information is not available for the live subject.

At block 502, a data collection engine 204 of a mobile computing device 102 uses a camera 202 of the mobile computing device 102 to capture one or more images of a live subject. Similar techniques may be used to capture the one or more images of the live subject as were used to capture the one or more images of the training subject at block 304, such as capturing single images or capturing a video and extracting images from the frames of the video.

In some embodiments, the mobile computing device 102 and camera 202 may match a type of mobile computing device 102 and/or camera 202 used at block 304 of method 300. For example, the mobile computing device of block 304 may be an iPhone 6, and the camera of block 304 may be the front-facing camera of the iPhone 6, while the mobile computing device of block 502 may be the same or a different iPhone 6, and the camera of block 502 may again be the front-facing camera. In some embodiments, the normalization steps and the machine learning model may be customized to the model of mobile computing device 102 and camera 202 used to collect the training data and the image of the live subject. In some embodiments, a different type of mobile computing device 102 and/or camera 202 may be used at block 304 than at block 502, and differences between the captured images may be minimized during normalization.

At block 504, the data collection engine 204 transmits the one or more images of the live subject to the skin color determination device 104. As above, the data collection engine 204 may transmit the images to the skin color determination device 104 using any suitable wired or wireless communication technology.

At block 506, the image normalization engine 212 normalizes the one or more images of the live subject. In some embodiments, the normalization of the images of the live subject matches the normalization that was performed on the images of the training subject at block 310. As one non-limiting example, the actions illustrated in FIG. 4 may be applied to the images of the live subject in a way that matches the actions applied to the images of the training subject.

At block 508, a skin color determination engine 210 of the skin color determination device 104 uses the normalized one or more images of the live subject and the one or more machine learning models to determine a skin color of the live subject. In some embodiments, the normalized one or more images of the live subject are provided as inputs to a first machine learning model to estimate an illuminant color, and then the normalized one or more images of the live subject and the illuminant color are provided as inputs to a second machine learning model to estimate the skin color. In some embodiments, the normalized one or more images of the live subject are provided as inputs to a single machine learning model that directly estimates the skin color. In some embodiments, multiple normalized images may be provided at once as input to a single machine learning model (or to a first machine learning model and then to a second machine learning model). In some embodiments, normalized images may be analyzed one at a time, and the estimated skin colors for the normalized images may be averaged or otherwise combined to generate a final skin color determination. In some embodiments, the images of the live subject may be processed by the machine learning models without normalization.

At block 510, the skin color determination engine 210 transmits the skin color to the mobile computing device 102. In some embodiments, the user interface engine 206 may present a name or value associated with the skin color to the user. In some embodiments, the user interface engine 206 may recreate the color for presentation to the user on a display of the mobile computing device 102.

At block 512, a product recommendation engine 214 of the skin color determination device 104 determines one or more products to recommend based on the skin color. At block 514, the product recommendation engine 214 transmits the one or more products to the mobile computing device 102. The user interface engine 206 may then present the products to the user, and may allow the user to purchase or otherwise obtain the products.

In some embodiments, the product recommendation engine 214 may determine one or more products in the product data store 220 that match the determined skin color. This may be particularly useful for products such as foundation that are intended to match the skin color of the user. In some embodiments, the product recommendation engine 214 may determine one or more products in the product data store 220 that complement the skin color but do not match the skin color. This may be particularly useful for products such as eye shadow or lip colors where matching the skin color exactly is less desirable. In some embodiments, the product recommendation engine 214 may use a separate machine learning model, such as a recommender system, to determine a product from the product data store 220 based on products preferred by other users with a matching or similar skin color. In some embodiments, if an existing product does not match the skin color, the product recommendation engine 214 may determine ingredients for creating a product that would match the skin color, and may provide the ingredients to a compounding system for creating a custom product that would match the skin color.

Figure 6:
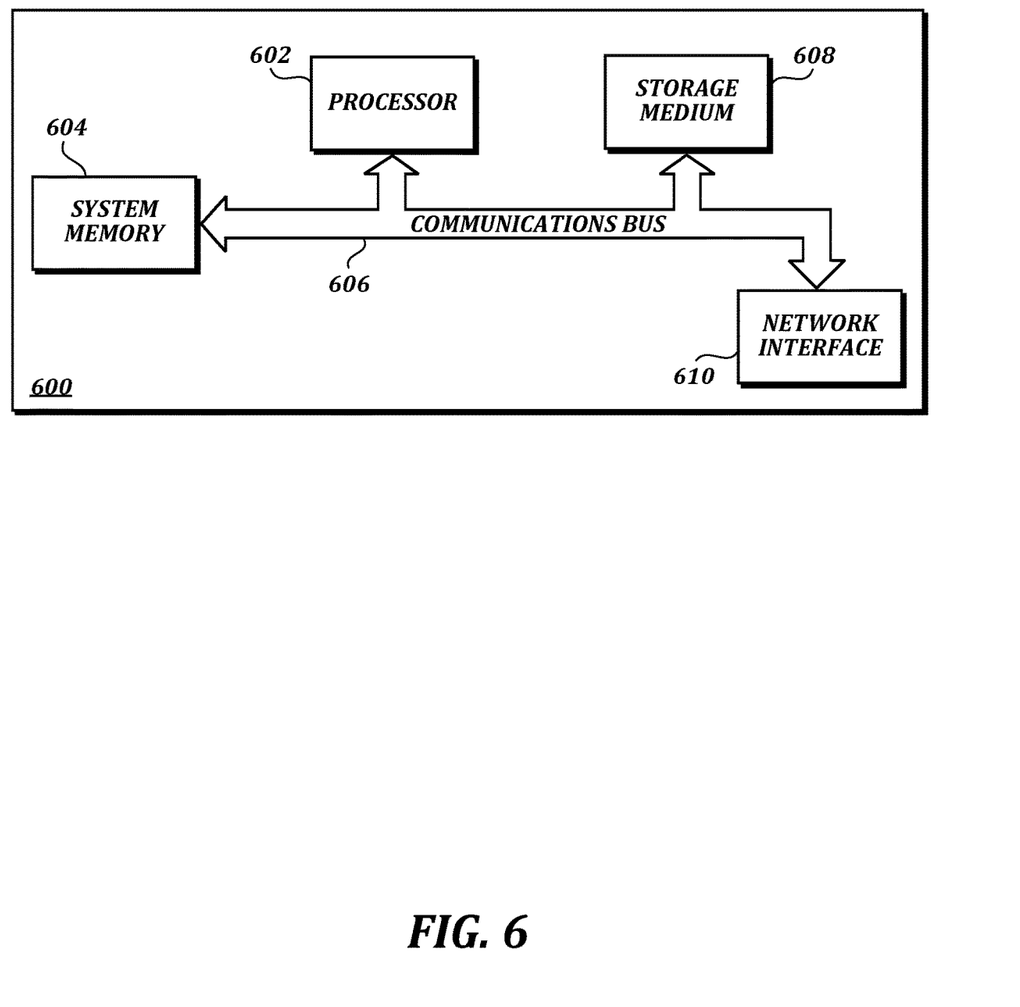
FIG. 6 is a block diagram that illustrates aspects of an exemplary computing device appropriate for use as a computing device of the present disclosure.

FIG. 6 is a block diagram that illustrates aspects of an exemplary computing device 600 appropriate for use as a computing device of the present disclosure. While multiple different types of computing devices were discussed above, the exemplary computing device 600 describes various elements that are common to many different types of computing devices. While FIG. 6 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 610 illustrated in FIG. 6 may represent one or more wireless interfaces or physical communication interfaces described and illustrated above with respect to particular components of the system 100.

In the exemplary embodiment depicted in FIG. 6, the computing device 600 also includes a storage medium 608. However, services may be accessed using a computing device that does not include means for persisting data to a local storage medium. Therefore, the storage medium 608 depicted in FIG. 6 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, tablet, and/or the like. Such input devices may be coupled to the computing device 600 by wired or wireless connections including RF, infrared, serial, parallel, Bluetooth, Bluetooth low energy, USB, or other suitable connections protocols using wireless or physical connections. Similarly, the computing device 600 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention. For example, while embodiments described above train and use models to estimate skin color, in some embodiments, skin features other than skin color may be estimate. For instance, in some embodiments, one or more machine learning models may be trained to estimate a Fitzpatrick skin type using techniques similar to those discussed above with respect to skin color, and such models may then be used to estimate Fitzpatrick skin types for images of live subjects.

Further, while embodiments described above train and use models that estimate a skin color for a whole face depicted in an image, in some embodiments, one or more convolutional neural network image classifiers may be trained and used to generate pixel-wise prediction scores for skin color of a face in an image. Such embodiments may include a system that comprises a skin color prediction unit including computational circuitry configured to generate the pixel-wise prediction score using the one or more convolutional neural network image classifiers, and a predicted skin color unit including computational circuitry configured to generate a virtual display of a predicted skin color of a user responsive to one or more inputs based on the prediction scores for the skin color of the face.

The invention claimed is:

1. A method of training a machine learning model to estimate a skin color of a face in an image, the method comprising:
  receiving, by a computing device, at least one training image that includes a face of a training subject and a color reference chart;
  receiving, by the computing device, tagging information for the at least one training image, wherein receiving the tagging information for the at least one training image includes:
    detecting, by the computing device, the color reference chart from the at least one training image that includes the face of the training subject; and
    determining, by the computing device, an illuminant color based on the color reference chart;
  adding, by the computing device, the at least one training image and the tagging information to a training data store; and
  training, by the computing device, the machine learning model to determine skin colors of faces using information stored in the training data store.

2. The method of claim 1, further comprising normalizing, by the computing device, the at least one training image to create at least one normalized training image.

3. The method of claim 2, wherein normalizing the at least one training image to create at least one normalized training image includes:

detecting, by the computing device, a face in the at least one training image;
centering, by the computing device, the face in the at least one training image; and
zooming, by the computing device, the at least one training image such that the face is a predetermined size.

4. The method of claim 1, wherein receiving at least one training image includes:
receiving, by the computing device, a video; and
extracting, by the computing device, at least one training image from the video.

5. The method of claim 1, further comprising adjusting, by the computing device, a color of the at least one training image based on the determined illuminant color.

6. The method of claim 1, wherein training the machine learning model to determine skin colors of faces using the training data set includes:
training, by the computing device, a first machine learning model that processes a training image as input to produce an indication of a lighting condition as an output; and
training, by the computing device, a second machine learning model that processes the training image and the indication of the lighting condition as input to produce an indication of skin color as an output.

7. A non-transitory computer-readable medium having computer-executable instructions stored thereon that, in response to execution by one or more processors of a computing device, cause the computing device to perform actions for training a machine learning model to estimate a skin color of a face in an image, the actions comprising:
receiving, by the computing device, at least one training image that includes a face of a training subject and a color reference chart;
receiving, by the computing device, tagging information for the at least one training image, wherein receiving the tagging information for the at least one training image includes:
detecting, by the computing device, the color reference chart from the at least one training image that includes the face of the training subject; and
determining, by the computing device, an illuminant color based on the color reference chart;
adding, by the computing device, the at least one training image and the tagging information to a training data store; and
training, by the computing device, the machine learning model to determine skin colors of faces using information stored in the training data store.

8. The computer-readable medium of claim 7, wherein the actions further comprise normalizing, by the computing device, the at least one training image to create at least one normalized training image.

9. The computer-readable medium of claim 8, wherein normalizing the at least one training image to create at least one normalized training image includes:
detecting, by the computing device, a face in the at least one training image;
centering, by the computing device, the face in the at least one training image; and
zooming, by the computing device, the at least one training image such that the face is a predetermined size.

10. The computer-readable medium of claim 7, wherein receiving at least one training image includes:
receiving, by the computing device, a video; and
extracting, by the computing device, at least one training image from the video.

11. The computer-readable medium of claim 7, wherein the actions further comprise adjusting, by the computing device, a color of the at least one training image based on the determined illuminant color.

12. The computer-readable medium of claim 7, wherein training the machine learning model to determine skin colors of faces using the training data set includes:
training, by the computing device, a first machine learning model that processes a training image as input to produce an indication of a lighting condition as an output; and
training, by the computing device, a second machine learning model that processes the training image and the indication of the lighting condition as input to produce an indication of skin color as an output.

13. A system for training a machine learning model to estimate a skin color of a face in an image, the system comprising:
circuitry for receiving at least one training image that includes a face of a training subject and a color reference chart;
circuitry for receiving tagging information for the at least one training image, wherein receiving the tagging information for the at least one training image includes:
detecting the color reference chart from the at least one training image that includes the face of the training subject; and
determining an illuminant color based on the color reference chart;
circuitry for adding the at least one training image and the tagging information to a training data store; and
circuitry for training the machine learning model to determine skin colors of faces using information stored in the training data store.

14. The system of claim 13, further comprising circuitry for normalizing the at least one training image to create at least one normalized training image.

15. The system of claim 14, wherein normalizing the at least one training image to create at least one normalized training image includes:
detecting a face in the at least one training image;
centering the face in the at least one training image; and
zooming the at least one training image such that the face is a predetermined size.

16. The system of claim 13, wherein receiving at least one training image includes:
receiving a video; and
extracting at least one training image from the video.

17. The system of claim 13, further comprising circuitry for adjusting a color of the at least one training image based on the determined illuminant color.

18. The system of claim 13, wherein training the machine learning model to determine skin colors of faces using the training data set includes:
training a first machine learning model that processes a training image as input to produce an indication of a lighting condition as an output; and
training a second machine learning model that processes the training image and the indication of the lighting condition as input to produce an indication of skin color as an output.

* * * * *